(12) United States Patent
Mangia et al.

(10) Patent No.: US 9,169,269 B2
(45) Date of Patent: Oct. 27, 2015

(54) WATER-SOLUBLE SOLID PHARMACEUTICAL INCLUSION COMPLEXES AND THEIR AQUEOUS SOLUTIONS FOR ORAL, OPHTHALMIC, TOPICAL OR PARENTERAL USE CONTAINING A MACROLIDE AND CERTAIN CYCLODEXTRINS

(75) Inventors: Alberto Mangia, Basigilio (IT); Paride Grisenti, Milan (IT); Elisa Verza, Corbetta (IT); Shahrzad Reza Elahi, Peschiera Borromeo (IT); Riccardo Monti, Milan (IT)

(73) Assignee: EUTICALS SPA, Milan (IT)

( * ) Notice: Subject to any disclaimer, the term of this patent is extended or adjusted under 35 U.S.C. 154(b) by 267 days.

(21) Appl. No.: 13/172,038

(22) Filed: Jun. 29, 2011

(65) Prior Publication Data
US 2012/0053198 A1    Mar. 1, 2012

(30) Foreign Application Priority Data
Jul. 1, 2010    (IT) .............................. MI2010A1212

(51) Int. Cl.
*A01N 43/42*    (2006.01)
*A61K 31/44*    (2006.01)
*C07D 498/18*    (2006.01)

(52) U.S. Cl.
CPC .................................. *C07D 498/18* (2013.01)

(58) Field of Classification Search
USPC ........................................................ 514/291
See application file for complete search history.

(56) References Cited

U.S. PATENT DOCUMENTS 5,024,998 A    6/1991    Bodor

FOREIGN PATENT DOCUMENTS

| EP | 0839028 | * | 1/2004 |
| EP | 0839028 | B1 | 1/2004 |
| EP | 1710244 | A1 | 10/2006 |
| EP | 2135601 | A1 | 12/2009 |
| WO | 2006026531 | A1 | 3/2006 |
| WO | 2006039237 | A1 | 4/2006 |
| WO | WO 2006/039237 | * | 4/2006 |
| WO | 2007011708 | A2 | 1/2007 |

OTHER PUBLICATIONS

Koontz et. al. (J. Agric. Food. Chem . (2003) 51:7106-7110).*
Vikmon (Proceedings of the Fourth International Symposium on Cyclodextrins (1988) 307-312).*
Arima et. al. (Journal of Pharmaceutical Sciences (2001) 90:69-701).*
Buech, G. et al., "Formulation of Sirolimus Eye Drops and Corneal Permeation Studies," Journal of Ocular Pharmacology and Therapeutics, vol. 23, No. 3, 2007, pp. 292-303.
Arima H. et al., "Comparative studies of the enhancing effects of cyclodextrins on the solubility and oral bioavailability of tacrolimus in rats," Journal of Pharmaceutical Sciences, American Pharmaceutical Association, Washington, US, vol. 90, No. 6, Jun. 1, 2001, pp. 690-701.
Koontz J. et al., "Formation of Natamycin: Cyclodextrin Inclusion Complexes and Their Characterization," Journal of Agricultural and Food Chemistry, American Chemical Society, US, vol. 51, No. 24, Nov. 19, 2003, pp. 7106-7110.
"European Search Report and Written Opinion dated Nov. 11, 2010 for IT MI20101212, from which the instant application is based," 11 pgs.
Cai, Ping et al., "In Vitro Metabolic Study of Temsirolimus: Preparation, Isolation, and Identification of the Metabolites," American Society for Pharmacology and Experimental Therapeutics, DMD Fast Forward, May 31, 2007.
Sedrani, Richard et al., "Dihydroxylation of the Triene Subunit of Rapamycin," J. Org. Chem. 1998, 63, 10069-10073.
Goulet, Mark T. et al., "Degradative Studies on the Tricarbonyl Containing Macrolide Rapamycin," Chim Bioc Biot M., Tetrahedron Letters 1990, 31(34), pp. 4845-4848.
Nickmilder, M.J.M. et al., "Isolation and identification of new rapamycin dihydrodiol metabolites from dexamethasone-induced rat liver microsomes," Xenobiotica, 1997, vol. 27, No. 9, pp. 869-883.
Il'Ichev, Yuri V. et al., "Degradation of rapamycin and its ring-opened isomer: role of base catalysis," ARKIVOC, 2007 (XII) pp. 110-131.

* cited by examiner

*Primary Examiner* — Marcos Sznaidman
(74) *Attorney, Agent, or Firm* — Fredrikson & Byron, P.A.

(57) ABSTRACT

This invention relates to new water-soluble solid pharmaceutical inclusion complexes and their aqueous solutions for oral, ophthalmic, topical or parenteral use containing a macrolide and certain cyclodextrins.
More particularly the invention relates to new water-soluble solid pharmaceutical inclusion complexes and their solutions in aqueous solvents, said compositions containing
  a) as an active ingredient a macrolide such as Rapamycin, Pimecrolimus, Temsirolimus, Everolimus or Tacrolimus in an amorphous form and optionally in the form of their polymorphic hydrates or solvates e.g. solvates formed with acetone or ethanol.
  b) a large surface cyclodextrin, such as gamma cyclodextrin—whereby the weight ratio of said macrolide to said cyclodextrin ranges between 1:111 and 1:333.

18 Claims, 23 Drawing Sheets

WATER-SOLUBLE SOLID PHARMACEUTICAL INCLUSION COMPLEXES AND THEIR AQUEOUS SOLUTIONS FOR ORAL, OPHTHALMIC, TOPICAL OR PARENTERAL USE CONTAINING A MACROLIDE AND CERTAIN CYCLODEXTRINS

CROSS REFERENCE TO RELATED APPLICATIONS

This application claims priority to Italian Patent Application No. MI2010A001212, filed on Jul. 1, 2010, which is incorporated herein by reference in its entirety.

FIELD

This invention relates to new water-soluble solid pharmaceutical inclusion complexes and their aqueous solutions for oral, ophthalmic, topical or parenteral use containing a macrolide and certain cyclodextrins.

STATE OF THE ART

The macrolides are a group of drugs (typically antibiotics) whose activity stems from the presence of a macrolide ring, a large macrocyclic lactone ring to which one or more deoxy sugars, may be attached. The lactone rings are usually 14, 15 or 16-membered. Macrolides belong to the polyketide class of natural products. Among this family, Sirolimus, also known as Rapamycin of formula 1, identified by the registry number 53123-88-9, and Tacrolimus of formula 2, identified by the registry number 104987-11-3, are compounds known for their immunosuppressive activity, and are used to prevent the rejection of organ and bone marrow transplants in the body.

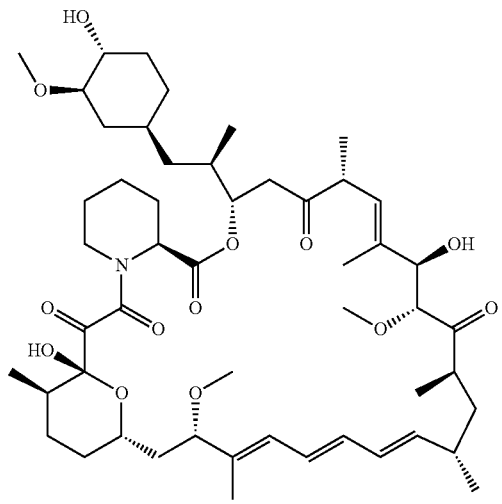

Formula 1

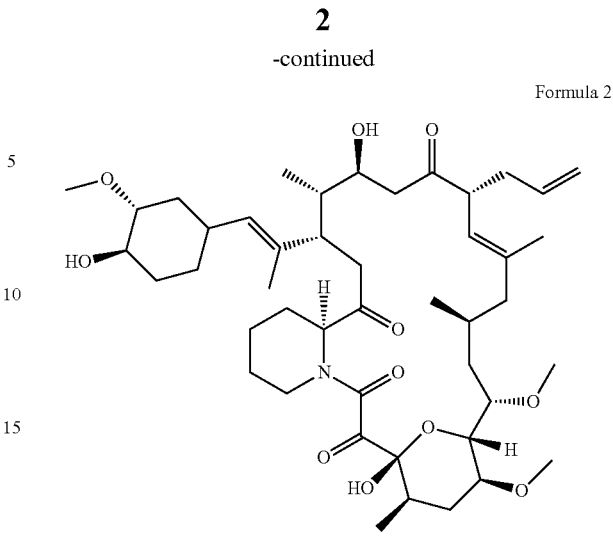

Formula 2

Rapamycin derivatives, such as Temsirolimus, Everolimus and Pimecrolimus, a synthetic derivative of Ascomycin, display a similar inhibitory activity for a specific protein (mTOR) involved in the regulation of cell growth, proliferation and survival.

Temsirolimus of formula 3, identified by the registry number 162635-04-3, is structurally related to Rapamycin and is used to treat advanced renal cell carcinoma (a type of kidney cancer). It is also being studied in the treatment of other types of cancer.

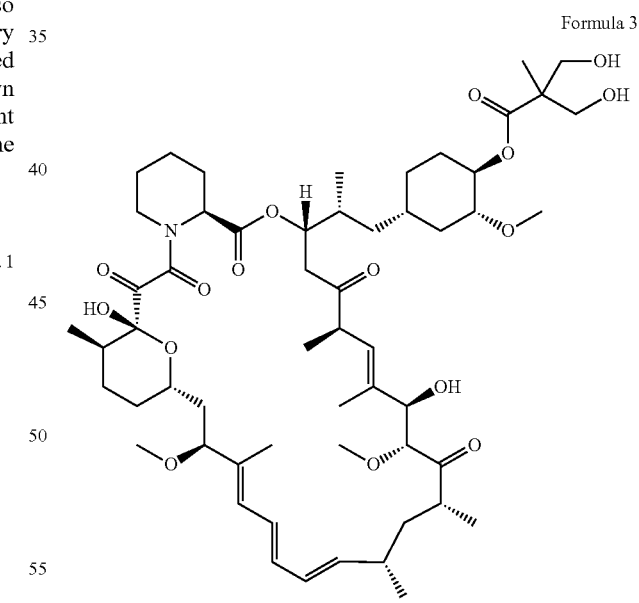

Formula 3

Everolimus of formula 4, identified by the registry number 159351-69-6, is used to treat advanced kidney cancer that did not respond to treatment with certain other anticancer drugs. It is also being studied in the treatment of other types of cancer like Waldenstrom's macroglobulemia or breast cancer.

Formula 4

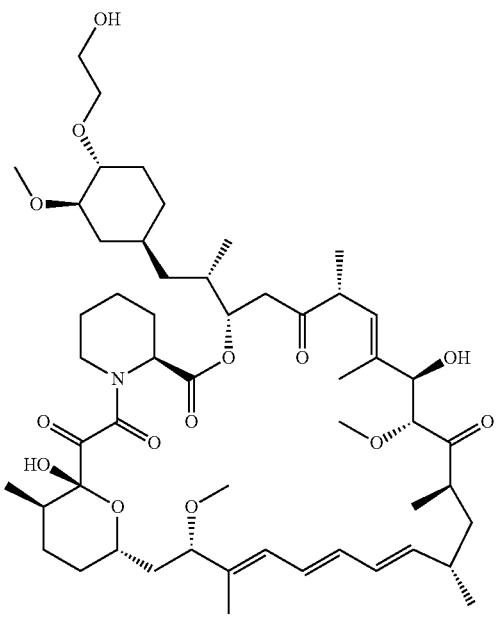

Pimecrolimus of formula 5, identified by the registry number 137071-32-0, a synthetic derivative of Ascomycin; is used for the treatment of atopic dermatitis.

Formula 5

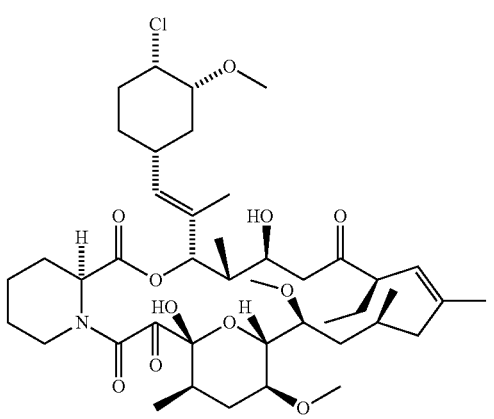

All these compounds have poor aqueous solubility at room temperature, ranging from 0.01 to 0.000006 mol/L, and are reported to be unstable in solution upon storage and, as a consequence of solvolysis, of its ester linkage leading to loss of biological activity both in vitro and in vivo (Yuri V. Il'ichev, Lori Alquier, and Cynthia A. Maryanoff, ARKIVOC, 2007 (XII) 110-131; Ping Cai, Rushung Tsao, and Mark E. Ruppen, DMD Fast Forward. May 31, 2007).

Moreover in the solid state these compounds may exist in amorphous or crystalline form, the amorphous one being very unstable to oxidative degradation (*Tetrahedron Letters* (1990), 31(34), 4845-8. *Xenobiotica*, 27(9), 869 (1997); *J. Org. Chem.*, 63, 10069, (1998)).

It is a common knowledge that amorphous forms have higher solubility (the solubility increase from crystalline to amorphous material has been reported to be between 10 and 1600 fold), are less stable, prone to degradation if compared to a crystalline form.

Moreover poor solubility is usually associated to poor absorption in the body and poor availability. U.S. Pat. No. 5,024,998 suggests that aqueous parenteral solutions of sparingly soluble drugs in water combined with cyclodextrins are able to minimize drug precipitation at injection sites or organs following parenteral application.

EP839028 describes the possibility to prepare a pharmaceutical composition for oral administration in the form of a solid dispersion of Rapamycin on alpha or beta cyclodextrin.

Actually, literature data confirms that finely micronized Rapamycin or amorphous Rapamycin need to be stabilized for formulation purposes using different coating techniques that foresee the use of several synthetic polymers, like polybutyl methacrylate (PBMA), polyethylene-co-vinyl acetate (PEVA), or polyelectrolyte complex like protamine sulfate and cellulose, as described in WO 2006026531, WO 2006039237, WO 2007011708 and EP 2135601.

These polymeric matrices however show poor water solubility or are polyelectrolyte, i.e. polymers that may be water soluble only in a narrow pH range. Moreover literature data does not report quantitative data on the stability of these complexes.

For the above cited reasons the possibility to increase the solubility and stability of macrolides through the use of a stabilized amorphous form in combination with a gamma cyclodextrin was explored.

DESCRIPTION OF THE INVENTION

The following definitions are used throughout the specification and claims.

The term "alpha Cyclodextrin", or "alpha CD" refers to the compound identified with registry number 10016-20-3, also called cyclomaltohexaose.

The term "beta Cyclodextrin", or "beta CD" refers to the compound identified with registry number 7585-39-9, also called cyclomaltoheptaose. The term "gamma Cyclodextrin", or "gamma CD" refers to the compound identified with registry number 17465-86-0, also called cyclomaltooctaose.

The term "amorphous" refers to a solid state of a compound that is non-crystalline.

The term "macrolide" as used herein, refers to Rapamycin, Temsirolimus, Everolimus, Pimecrolimus and Tacrolimus.

The aim of the present invention was to improve both stability and solubility of macrolides when adsorbed on cyclodextrin, by formation of an inclusion complex.

As it is well known to those skilled in the art these complexes often display altered physicochemical properties compared to the guest molecule, such as increased aqueous solubility, stability, or bioavailability.

An object of the present invention is thus to provide inclusion complexes of macrolides with gamma cyclodextrin, that may be used for formulation purposes while possibly decreasing toxicity of accompanying materials usually employed for formulation purposes.

Actually, it has been surprisingly found that gamma cyclodextrins exhibit a positive effect on the stability of macrolides and prevent precipitation from oversaturated aqueous solutions without using an organic solvent as a co-solvent.

Another object of the present invention is therefore an aqueous solution of these complexes, which does not contain any organic solvent.

A further object of the present invention is the use of these complexes to prepare oral, ophthalmic, topical and injectable formulations, as well as the use of such complexes and/or formulations as immunosuppressive agents.

In order to proceed with formulative studies we have performed preliminary stability tests on micronized Rapamycin ($10^{-5}$ microns) and in solution (ethanol).

The results obtained by us confirmed that this product finely micronized and in solution is unstable: within few hours we observed a sensible decrease (−10%) in the assay value.

Several attempts were made by us in order to stabilize amorphous Rapamycin, or finely micronized Rapamycin, from degradation without success: the addition of antioxidants, like alpha tocoferol and ascorbic acid, were unable to control this degradation even working under inert atmosphere (nitrogen) and in refrigerated conditions (0-4° C.).

This behaviour was observed only on micronized Rapamycin below 20 microns, on amorphous Rapamycin and in solution but not on crystalline Rapamycin with a larger particle size (i.e. >100 micron).

Figure 1:
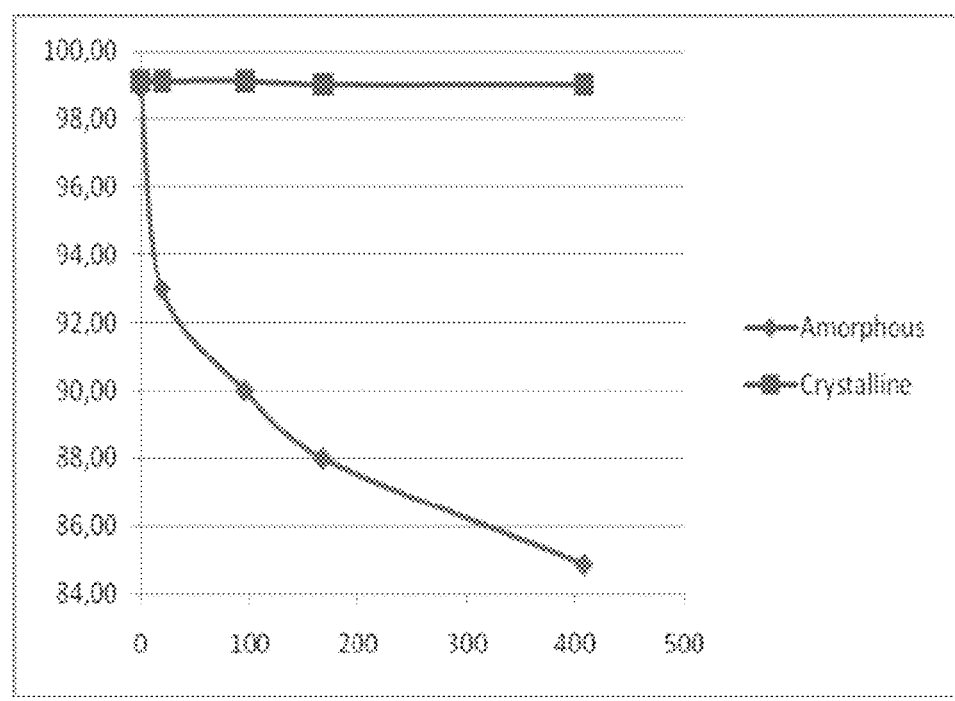
FIG. 1: Decrease of the chromatographic purity (HPLC data) of amorphous Rapamycin and of crystalline Rapamycin (60° C. for 17 days (408 hours))

On table 1 and in the corresponding FIG. 1 the stability data obtained at 60° C. on Rapamycin in an amorphous and in a crystalline form (products with a particle size>100 micron) is reported: while crystalline Rapamycin presents after 408 hours (17 days) the same chromatographic purity, amorphous Rapamycin shows a decrease of −14% of chromatographic purity.

TABLE 1

Decrease of the chromatographic purity (HPLC data; area %) of amorphous Rapamycin and of crystalline Rapamycin (60° C. for 17 days (408 hours))

| Hours | Amorphous Rapamycin | Crystalline Rapamycin |
|---|---|---|
| 0 | 98.90 | 99.10 |
| 20 | 93.00 | 99.10 |
| 96 | 90.00 | 99.10 |
| 168 | 88.00 | 99.00 |
| 408 | 84.90 | 99.00 |

We have verified that the same degradation occurs even on some synthetic derivatives of Rapamycin (i.e. Temsirolimus and Everolimus) and also on Pimecrolimus and Tacrolimus.

In order to overcome these stability problems we decided to study the possibility to stabilize these macrolides from degradation through the formation of a complex with commercially available cyclodextrins and, among several compounds of this family, of alpha cyclodextrin (alpha CD), beta cyclodextrin (beta CD) and gamma cyclodextrin (gamma CD). These cyclic oligosaccharides have the common feature to be composed of 6, 7 and 8 α-D-glucopyranoside units linked 1→4.

A preliminary study on the HPLC chromatographic mobility of these macrolides in presence of cyclodextrins confirms that the interaction between these macrolides and cyclodextrin was very weak.

The first macrolide evaluated by us was Rapamycin adsorbed on alpha cyclodextrin (alpha CD), beta cyclodextrin (beta CD) and gamma cyclodextrin (gamma CD).

In order to prepare these complexes, Rapamycin was dissolved in organic solvent, preferably a polar organic solvent, selected between acetone, methanol and ethanol, then these solutions were mixed with the cyclodextrins. In order to obtain a water soluble complex, the weight ratio between Rapamycin, or one of its derivatives, and a cyclodextrin is advantageously comprised between 1:100 and 1:400, more preferably between 1:111 and 1:333. Then the obtained heterogeneous mixture carefully evaporated under vacuum to afford the complexes as a solid powder; the wet solid powder was then dried under vacuum.

Suitable alternatives to the evaporation under vacuum of the heterogeneous mixture of Rapamycin and cyclodextrins were realized with the spray-dryer technique, by direct filtration of the suspension or by freeze drying. Said filtration can be optionally performed by diluting said heterogeneous mixture with an organic solvent, preferably an apolar organic solvent, more preferably a $C_5$-$C_8$ linear or branched hydrocarbon.

The obtained complexes were first evaluated for the stability in solution at 20-25° C. and as solid powder stored at −20° C.

The stability data in solution (water/acetonitrile 1/1 v/v mixture) indicates that, among the evaluated cyclodextrins complexes, the gamma CD complex shows at time zero the higher content of Rapamycin; moreover gamma CD and beta CD complexes after 19 days in solution at 20-25° C., do not show a decrease from the initial assay value while, in the same storage conditions, alpha CD complex shows a decrease in the assay value of −24% (Table 2 in the Experimental Section).

The stability data obtained on the solid complexes (powder) stored at −20° C. after 26 days shows a decrease in the assay value of −12% for alpha CD and −5.4% for beta CD while the Rapamycin content of gamma CD complex is, in the same experimental conditions, unchanged (Table 3 in the Experimental Section).

Surprisingly, in spite of the chemical likeness of the employed cyclodextrins which differs only of 1 and 2 α-D-glucopyranoside units, only the gamma CD complex with Rapamycin showed good stability data both in solution and in the solid form.

These preliminary data were further confirmed in the solid state (powder) in different storage conditions: at 25° C. (60% relative humidity) and at 40° C. (75% relative humidity) after 5 and 15 days (Tables 4 and 5 in the Experimental Section).

It was therefore confirmed that not only Rapamycin gamma CD complex was more stable of alpha and beta CD complexes, both at 25° C. and at 40° C., but that the release of Rapamycin from gamma CD complex at 40° C. was nearly quantitative (95% of recovery of the Rapamycin loaded on CD).

On the basis of these data we surprisingly found that, in our experimental conditions, only gamma CD was able to stabilize Rapamycin from degradation, both in solution and in solid state while alpha and beta CD complexes with Rapamycin were unstable.

Literature data does not describe the possibility to stabilize Rapamycin from degradation through the formation of a labile complex with gamma CD. Moreover this peculiar behaviour of gamma cyclodextrin is quite different from the parent compounds alpha and beta CD which, from a structural point of view are very similar and often considered equivalent to be utilized for formulative purposes.

This possibility to stabilize Rapamycin to degradation through a complex with gamma CD was further explored by us on Everolimus, Temsirolimus, Tacrolimus and Pimecrolimus showing that these structurally related compounds have a common behaviour: while the pure compound in an amorphous form, or finely micronized (i.e. with a particle size distribution of $10^{-5}$ microns), is unstable, the corresponding gamma CD complex is stable both in solution and in the solid state.

Figure 3:
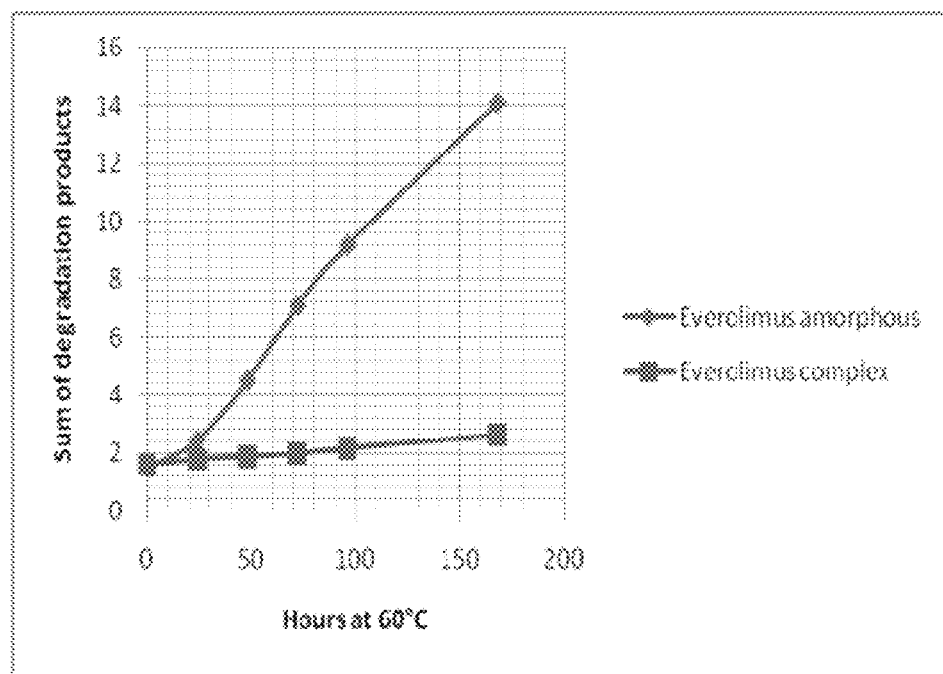
FIG. 3: Stability of Everolimus gamma CD/complex prepared using acetone as solvent versus amorphous Everolimus.

On FIG. 3 and Table 7 we have reported the stability data of Everolimus complex versus amorphous Everolimus: after 96 hours at 60° C. the increase of the degradation related by products on Everolimus complex is of +36% while on amorphous Everolimus is of +513%. Similar data were obtained for gamma CD Temsirolimus complex and gamma CD Pimecrolimus complex.

The analytical data performed on these complexes comprise HPLC/MS, HPLC/UV characterization (see FIGS. 4-13) and X-Ray diffraction data (DRX; see FIGS. 14-23): these analytical data confirm that the employed absorption technique does not modify the impurity profile of the macrolides and the solid state of gamma CD while all the evaluated macrolides after solvent treatment are in a prevalent amorphous form. The DRX data produced on the obtained complexes confirm that the macrolides are present in a prevalent amorphous form.

Finally for all the examined macrolides complexes with gamma CD we have verified a sensible increase in water solubility from the original macrolides; as indicated in table 8 below.

TABLE 8

Water solubility (data in mol/L, determined at 20-25° C.) of macrolide gamma CD complexes versus the corresponding macrolide utilized as starting material;

| | Water solubility (mol/L) of the starting material (macrolide)* | Water solubility (mol/L) of macrolide gamma CD complexes |
|---|---|---|
| Rapamycin | $6.7 \times 10^{-4}$ | >0.01 |
| Temsirolimus | 0.011 | >0.01 |
| Everolimus | $1.9 \times 10^{-3}$ | >0.01 |
| Tacrolimus | $7 \times 10^{-5}$ | $>5 \times 10^{-3}$ |
| Pimecrolimus | $5.3 \times 10^{-6}$ | $>0.4 \times 10^{-4}$ |

*Calculated using Advanced Chemistry Development (ACD/Labs) Software V8.14

EXPERIMENTAL SECTION

Materials and Methods

Rapamycin, Temsirolimus, Everolimus, Tacrolimus and Pimecrolimus were prepared by POLI INDUSTRIA CHIMICA SpA. Alpha cyclodextrin (Alpha CD), beta cyclodextrin (beta CD) and gamma cyclodextrin (gamma CD) were purchased by Fluka.

The HPLC methods used for the determination of assay and purity for Rapamycin, Temsirolimus, Everolimus, Tacrolimus and Pimecrolimus are reported herein.

For the HPLC determination of chromatographic purity of Rapamycin: Column: Thermo BDS Hypersil C18; 3 µm (100×4.6 mm). Mobile Phase composition: isocratic elution Component A: 50% acetonitrile Component B: 50% ammonium acetate buffer pH 5.8 (concentration 0.8 g/l of ammonium acetate; the final pH value was brought to a final value of 5.8 with glacial acetic acid)

Flow rate: 1.0 ml/min. Column temperature: 55° C. Volume of injection: 100 µl.

Sample solution: weight 25 mg of Rapamycin and dissolve in 100 ml of acetonitrile/water 1/1 v/v (final concentration 0.25 mg/ml). UV detector: 278 nm For the HPLC assay determination of Rapamycin: Column: Hypersil BDS-C18; 3 µm (100×4.6 mm). Mobile Phase composition: isocratic elution Component A: 58% acetonitrile Component B: 42% ammonium acetate buffer pH 5.8 (concentration 0.8 g/l of ammonium acetate; the final pH value was brought to a final value of 5.8 with glacial acetic acid)

Flow rate: 1.5 ml/min. Column temperature: 55° C. Volume of injection: 30 µl

Sample and standard solution: prepare a mother solution at the concentration of 0.25 mg/ml in acetonitrile/water 1/1, then dilute with mobile phase to obtain a final concentration of 20 micrograms/ml. UV detector: 278 nm For the HPLC determination of the chromatographic purity of Temsirolimus and Everolimus: Column: Zorbax SB-C18; 3.5 µm (75×4.6 mm), Precolumn: Symmetry Shield RP18; 5 µm (20×3.9 mm).

Mobile Phase composition:

Component A: 900 ml of water, 100 ml of acetonitrile and 50 µl of 50% aqueous acetic acid Component B: 1000 ml of acetonitrile and 50 µl of 50% aqueous acetic acid Gradient elution:

| Time (min) | Component A | Component B |
|---|---|---|
| 0 | 60 | 40 |
| 10 | 55 | 45 |
| 25 | 30 | 70 |
| 65 | 30 | 70 |
| 66 | 60 | 40 |
| 70 | 60 | 40 |

Flow rate: 1 ml/min. Column temperature: 60° C. Volume of injection: 20 µl.

Sample preparation: solution of 0.5 mg/ml in acetonitrile. Detector UV: 278 nm

For the HPLC determination of chromatographic purity of Pimecrolimus: Column: YMC ODS AQ, 5 µm (250×4.6 mm). Mobile Phase composition: isocratic elution with 70/30 Acetonitrile/0.01 M phosphate buffer (pH 2.5).

Flow rate: 1.2 ml/min. Column temperature: 60° C. Sample temperature 10° C.

Volume of injection: 10 µl. Sample solution: prepare a 0.5 mg/ml solution of Pimecrolimus in acetonitrile. Detector UV: 210 nm For the HPLC determination of chromatographic purity of Tacrolimus Column: Symmetry C18; 3.5 µm (150×2.1 mm). Mobile Phase composition: isocratic elution Component A: 58% of 0.1% aqueous acetic acid solution Component B: 15% acetonitrile Component C: 27% tetrahydrofuran Flow rate: 0.3 ml/min. Column temperature: 50° C. Volume of injection: 10 µl.

Sample solution: weight 25 mg of Tacrolimus and dissolve in 25 ml of acetonitrile/water 1/1 v/v (final concentration 1 mg/ml). Detector UV: 278 nm The Mass spectrometer utilized is a ion trap Agilent Mod. 6300 in positive ionization.

The Spray Dryer equipment utilized is a Buchi model B290 equipped with an Advance inert loop B-295 device.

DRX spectra (powder) were registered using a Diffractometer (PW1710 Philips) from a start angle [½ 2θ] of 5000 to 60000. The diffraction diagrams were obtained employing a Cu anode (Kα=1.54060 Å and Kα=1.54439 Å) without any physical treatment of the samples.

EXAMPLE 1

Preparation of Reconstitutable, Solid Rapamycin/Cyclodextrin Complex by Drying; (Ethanol 95%) as Solvent A 0.4% w/v solution of Rapamycin in Ethanol (96%) was added to cyclodextrin powder. The final relative ratio between Rapamycin and Cyclodextrin are reported in the tables 2 and 3.

This suspension was maintained under stirring at 20-25° C. for 30 minutes then the obtained mixture was dried under vacuum for 18 hours in order to remove the ethanol. The dry solid powder was stored at −20° C. under nitrogen atmosphere.

On table 2 the assay data (HPLC data) of Rapamycin/CD complexes in solution (1/1 water/acetonitrile mixture) is reported at 20-25° C. at t=0 and after 19 days.

TABLE 2

Stability of Rapamycin/CD in solution (1/1 water/acetonitrile) at t = 0 and after 19 days stored at 20-25° C.

| | % of Rapamycin on CD (% of recovery calculated on the amount of Rapamycin loaded) | | |
|---|---|---|---|
| Time (days) | Alpha CD | Beta CD | Gamma CD |
| Initial amount loaded | 0.63 | 0.63 | 0.60 |
| 0 | 0.41 (65.6%) | 0.37 (59.2%) | 0.43 (71.67%) |
| 19 | 0.31 (49.60%) | 0.37 (59.20%) | 0.43 (71.67%) |
| Decrease in the assay value after 19 days (%) | −24.39 | 0 | 0 |

On table 3 are reported the assay data (HPLC data) of Rapamycin/CD complexes (powder) stored at −20° C. at t=0 and after 26 days.

TABLE 3

Stability of Rapamycin/CD (powder) at t = 0 and after 26 days stored at −20° C.

| | % of Rapamycin on CD (% of recovery calculated on the amount of Rapamycin loaded) | | |
|---|---|---|---|
| Time (days) | Alpha CD | Beta CD | Gamma CD |
| Initial amount loaded | 0.63 | 0.63 | 0.60 |
| 0 | 0.41 (65.6%) | 0.37 (59.2%) | 0.43 (71.67%) |
| 26 | 0.36 (57.6%) | 0.35 (56.0%) | 0.43 (71.67%) |
| Decrease in the assay value after 26 days (%) | −12.2 | −5.4 | 0 |

Further stability data of Rapamycin/Cyclodextrin complex (powder) stored at 25° C. (60% RU) and at 40° C. (75% RU) after 5 and 15 days are reported respectively on tables 4 and 5. In these tables are reported the HPLC assay values.

TABLE 4

Stability data of Rapamycin/cyclodextrin complex at 25° C., 60% RU (the data reported is assay data in % area)
Stability data at 25° C., 60% RU

| | Time = 0 | Time = 5 days | Time = 15 days | Time = 15 days (repeated) |
|---|---|---|---|---|
| Alpha CD | 0.38 | 0.32 | 0.33 | 0.34 |
| Beta CD | 0.36 | 0.31 | 0.30 | 0.31 |
| Gamma CD | 0.37 | 0.46 | 0.41 | 0.42 |

TABLE 5

Stability data of Rapamycin/cyclodextrin complex at 40° C. (the data reported are assay data in % area)
Stability data 40° C., 75% RU

| | Time = 0 | Time = 5 days | Time = 15 days | Time = 15 days (repeated) |
|---|---|---|---|---|
| Alpha CD | 0.38 | 0.64 | 0.53 | 0.55 |
| Beta CD | 0.36 | 0.48 | 0.41 | 0.42 |
| Gamma CD | 0.37 | 0.42 | 0.50 | 0.52 |

EXAMPLE 2

Preparation of Reconstitutable, Solid Rapamycin/Cyclodextrin Complex by Drying; Acetone as Solvent A 0.4% w/v solution of Rapamycin in acetone was added to gamma cyclodextrin. The final relative ratio between Rapamycin and Cyclodextrin was 0.6% w/w. The obtained suspension was maintained under stirring at 20-25° C. for 30'. The obtained mixture was dried under vacuum for 18 hours in order to remove acetone Optionally the wet solid may be recovered by dilution of the suspension with n-heptane and filtration; then transferred into a drier.

The dry solid powder was stored at −20° C. under nitrogen atmosphere.

Figure 2:
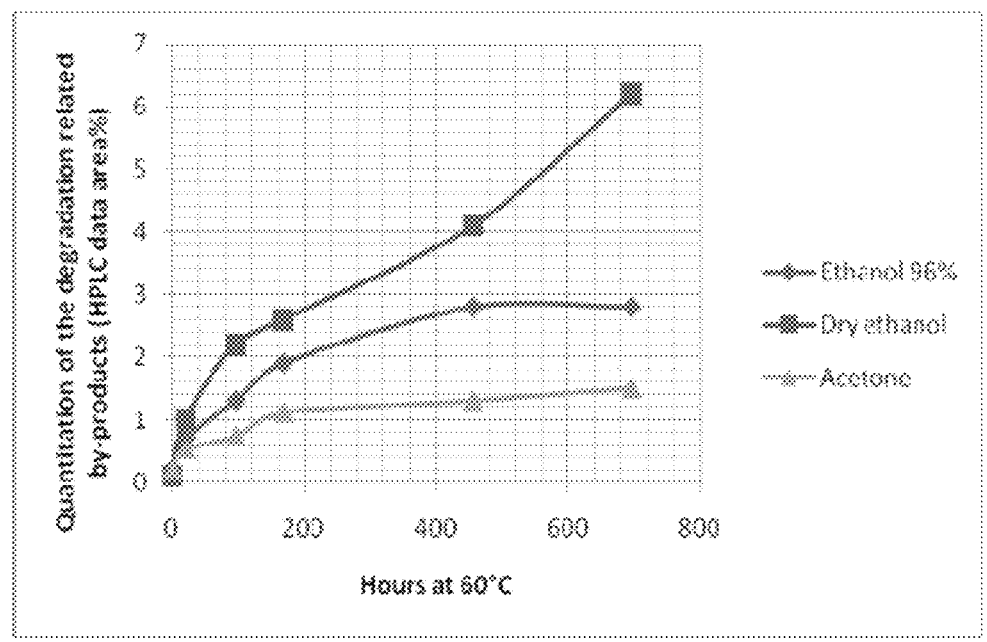
FIG. 2: Stability of Rapamycin gamma CD/complex prepared using different solvents: anhydrous ethanol, ethanol 96% and acetone.

The stability data of the obtained Rapamycin/gamma CD complex (powder) at 60° C. was compared with those obtained using as solvents dry ethanol and ethanol 96%; the obtained data is summarized on FIG. 2 and Table 6. In particular, in FIG. 2 the sum of the related by products originated by degradation (HPLC data) during a stability test performed on the powder at 60° C. for 696 hours is reported.

TABLE 6

Stability of Rampamycin gamma CD/complex prepared using different solvents: anhydrous ethanol, ethanol 96% and acetone. In this table the sum of the related by products originated by degradation (HPLC data) during stability tests performed on the powder at 60° C. for 696 hours is reported.

| Time (hours) | Ethanol 96% | Dry ethanol | Acetone |
|---|---|---|---|
| 0 | 0.2 | 0.1 | 0.2 |
| 20 | 0.7 | 1 | 0.5 |
| 96 | 1.3 | 2.2 | 0.7 |
| 168 | 1.9 | 2.6 | 1.1 |
| 456 | 2.8 | 4.1 | 1.3 |
| 696 | 2.8 | 6.2 | 1.5 |

EXAMPLE 3

Preparation of Reconstitutable, Solid Rapamycin/Cyclodextrin Complex by Spray-dryer; Acetone as Solvent A 0.1% w/v solution of Rapamycin in acetone was added to gamma cyclodextrin. The final relative ratio between Rapamycin and Cyclodextrin was 0.6% w/w. The obtained suspension was maintained under stirring at 20-25° C. for 30'.

The obtained suspension was treated with a spray-dryer in the followed experimental conditions:

Inlet nitrogen temperature=70° C.
Feed rate=17 ml/min
Outlet nitrogen temperature=54° C.
Aspirator speed=80%
Frequency of nozzle cleaning=2 shot/second The obtained solid powder was dried at 30° C. for 8 hours then stored at −20° C. under nitrogen atmosphere. The characteristics of this complex are the same described for the products obtained in the Example 2.

Preparation of Gamma CD Everolimus Complex, Gamma CD Temsirolimus Complex Gamma CD Tacrolimus Complex and Gamma CD Pimecrolimus Complex These complexes were prepared according to each of the examples 2 and 3.

HPLC UV and MS Data of Gamma CD Rapamycin Complex, Gamma CD Everolimus Complex, Gamma CD Temsirolimus Complex, Gamma CD Pimecrolimus Complex, Gamma CD Tacrolimus Complex and of the Corresponding Macrolides Utilized as Starting Material The HPLC profiles (HPLC and UV detector) of all the complexes are collected in the FIGS. 4-8. For each complex we have utilized the specific HPLC chromatographic conditions described in the experimental section.

Figure 4:
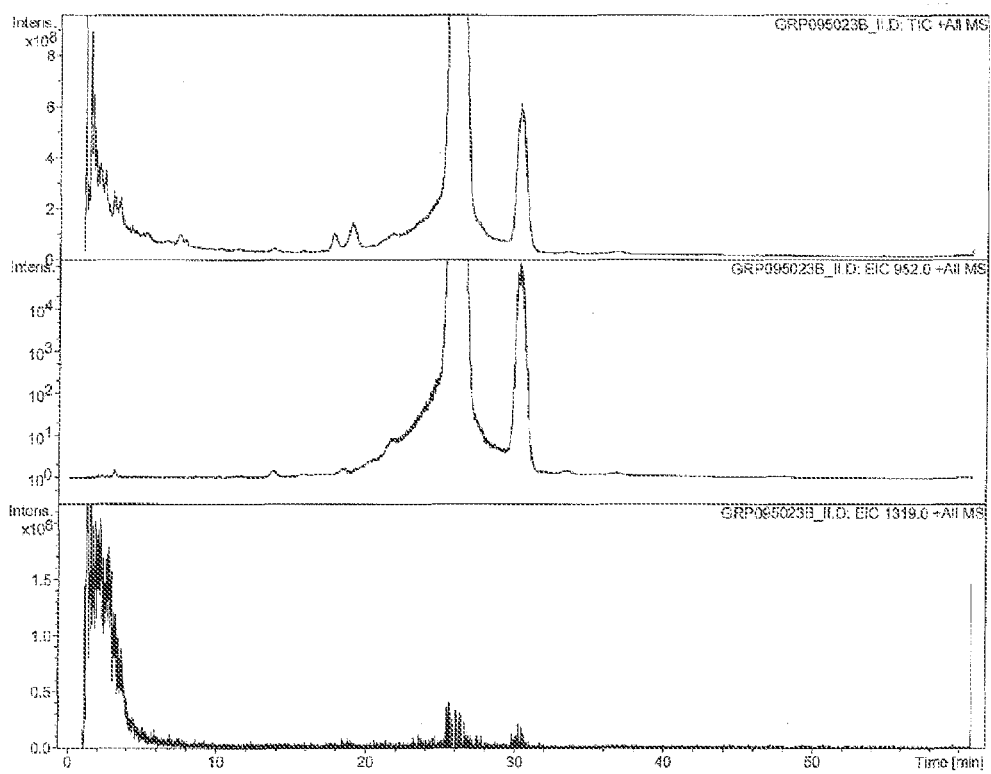
FIG. 4: HPLC/MS profile of Rapamycin gamma CD complex

FIG. 4. Rapamycin gamma CD complex=the total ion current (TIC), the single ion at m/z=952 (adduct of the molecular ion of Rapamycin with potassium; m/z=952), the single ion at m/z=1319 (adduct of gamma cyclodextrin with sodium; m/z=1319)

Figure 5:
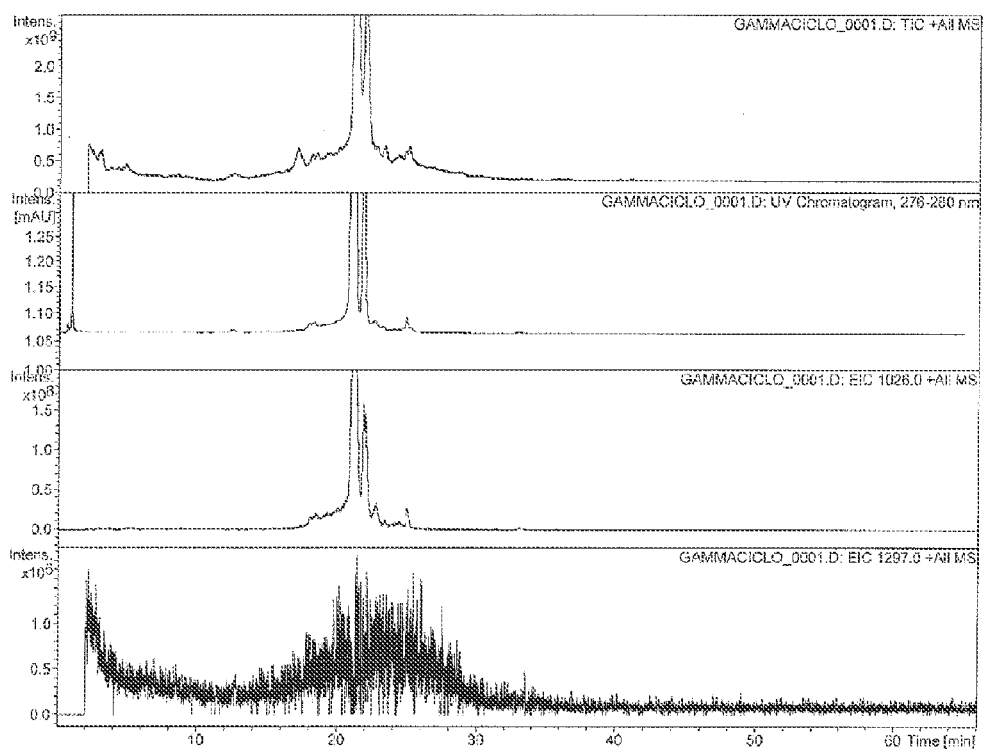
FIG. 5: HPLC/MS profile of Everolimus gamma CD complex

FIG. 5. Everolimus gamma CD complex=the total ion current (TIC), the spectrum UV (278 nm), the single ion at m/z=1026 (adduct of the molecular ion of Everolimus with potassium), the single ion at m/z=1297 (molecular ion of gamma cyclodextrin)

Figure 6:
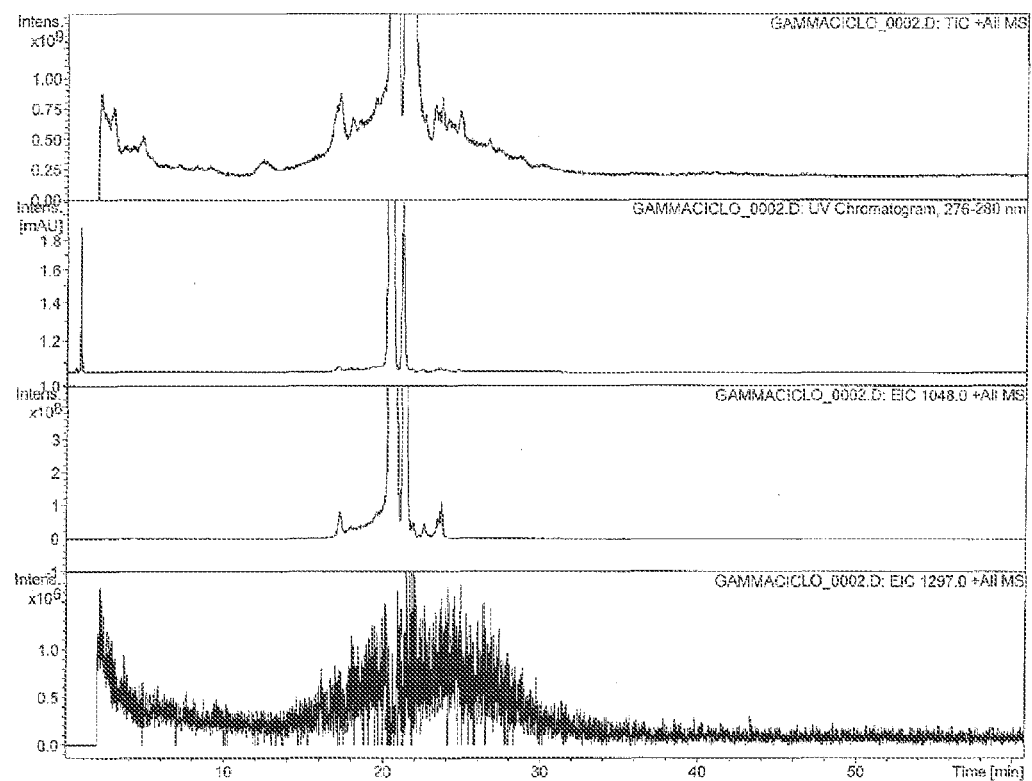
FIG. 6: HPLC/MS profile of Temsirolimus gamma CD complex

FIG. 6. Temsirolimus gamma CD complex=the total ion current (TIC), the spectrum UV (278 nm), the single ion at m/z=1048 (adduct of the molecular ion of Temsirolimus with ammonia), the single ion at m/z=1297 (molecular ion of gamma cyclodextrin)

Figure 7:
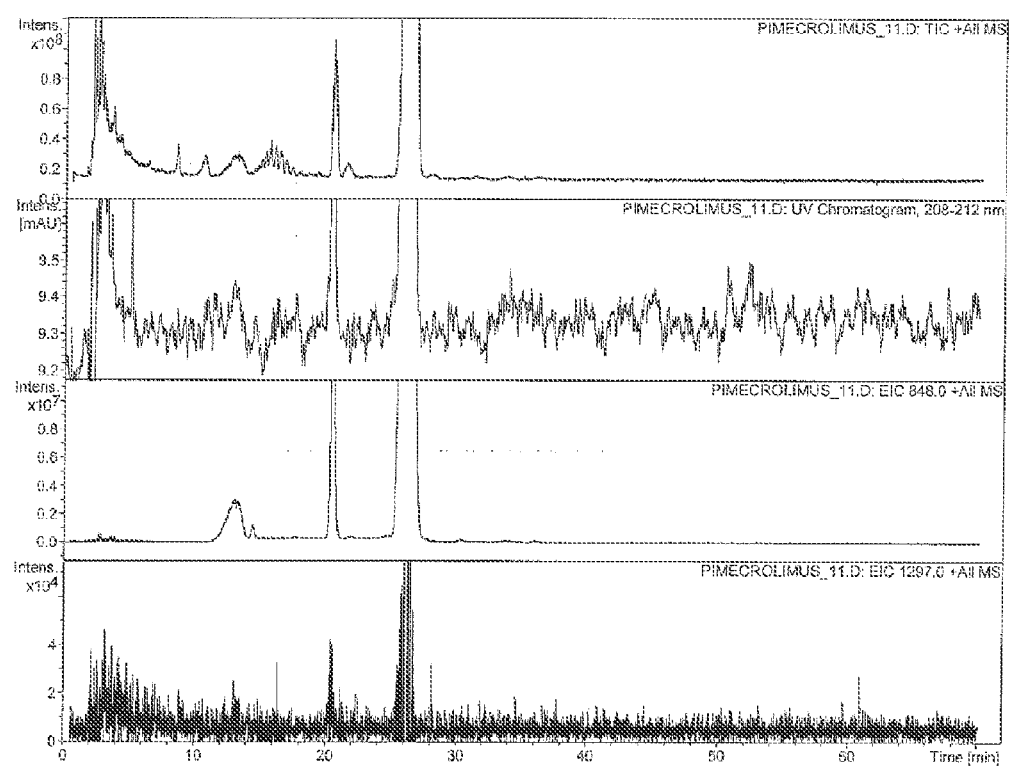
FIG. 7: HPLC/MS profile of Pimecrolimus gamma CD complex

FIG. 7. Pimecrolimus gamma CD complex=the total ion current (TIC), the spectrum UV (210 nm), the single ion at m/z=848 (adduct of the molecular ion of Pimecrolimus with potassium), the single ion at m/z=1297 (molecular ion of gamma cyclodextrin)

Figure 8:
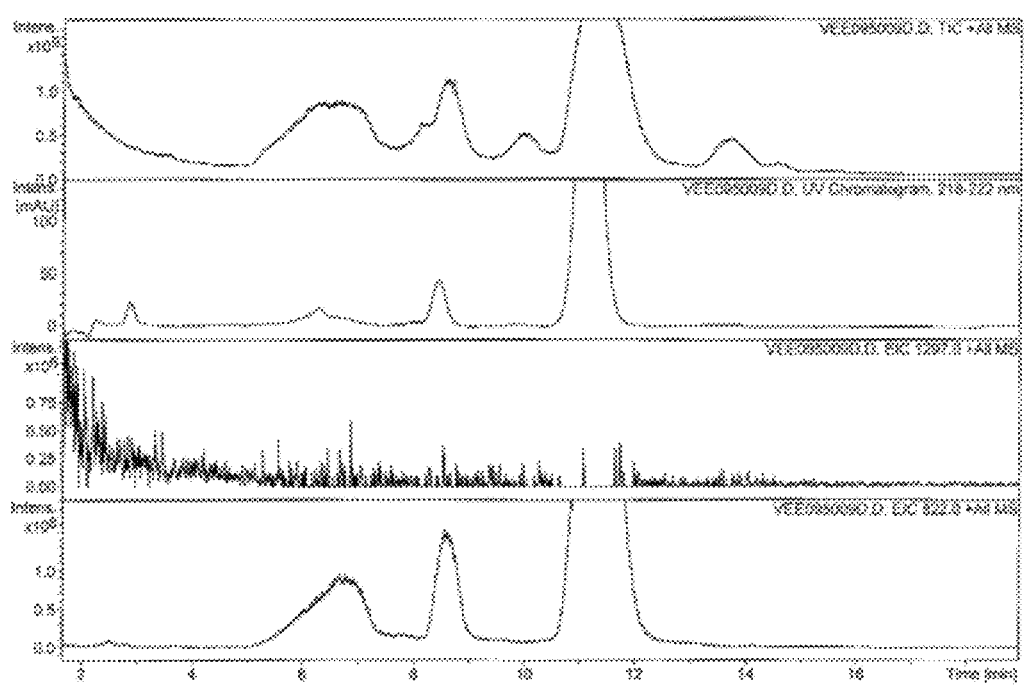
FIG. 8: HPLC/MS profile of Tacrolimus gamma CD complex

FIG. 8. Tacrolimus gamma CD complex=the total ion current (TIC), the spectrum UV (220 nm), the single ion at m/z=1297 (molecular ion of gamma cyclodextrin), the single ion at m/z=822 (adduct of the molecular ion of Tacrolimus with water)

The HPLC UV and MS chromatographic profile of these macrolides complex at t=0 was found unchanged from the corresponding macrolide utilized as starting material.

The HPLC/MS and HPLC/UV analyses of each macrolide utilized as starting material for the preparation of the CD complexes are here reported.

Figure 9:
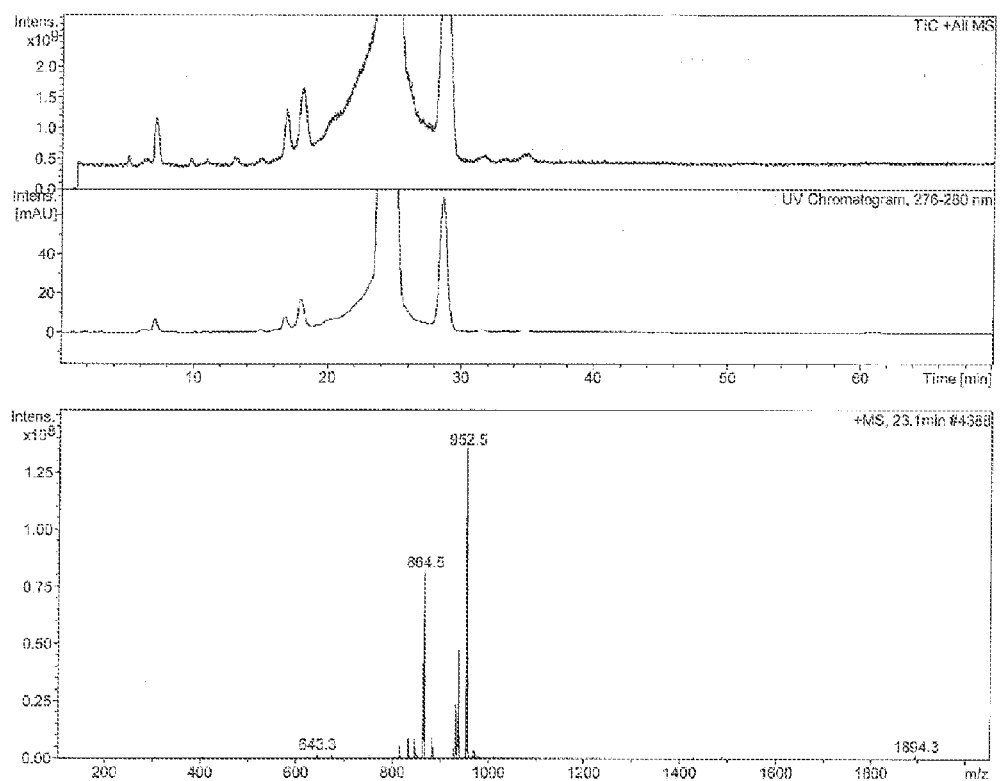
FIG. 9: HPLC/UV and HPLC/MS profiles of Rapamycin

FIG. 9. Rapamycin=the total ion current (TIC), the HPLC/UV profile and the mass spectrum of the main Rapamycin isomer eluted at 23'.

Figure 10:
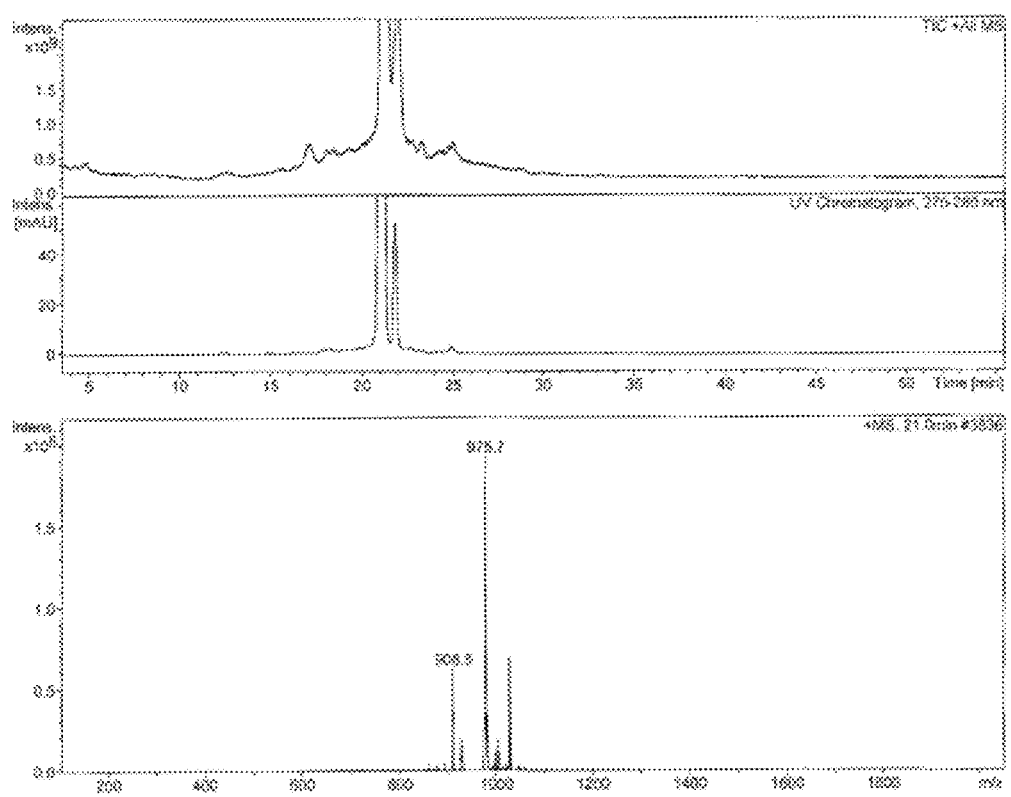
FIG. 10: HPLC/UV and HPLC/MS profiles of Everolimus

FIG. 10. Everolimus=the total ion current (TIC), the HPLC/UV profile and the mass spectrum of the main Everolimus isomer eluted at 21'.

Figure 11:
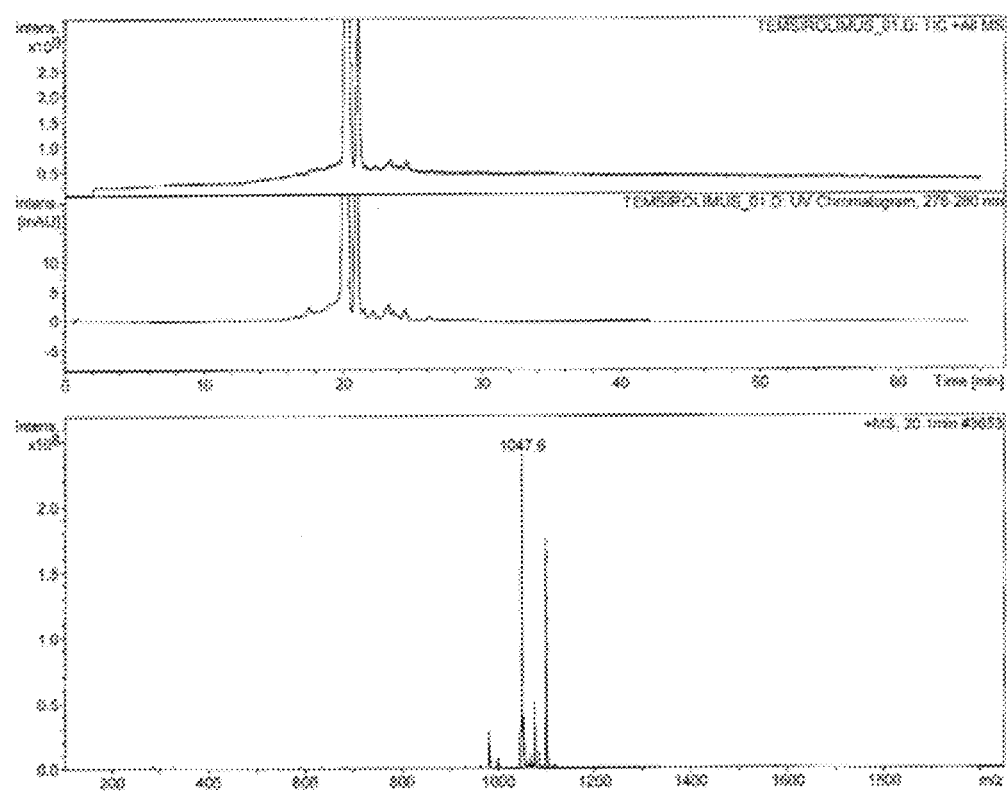
FIG. 11: HPLC/UV and HPLC/MS profiles of Temsirolimus

FIG. 11. Temsirolimus=the total ion current (TIC), the HPLC/UV profile and the mass spectrum of the main Temsirolimus isomer eluted at 20'

Figure 12:
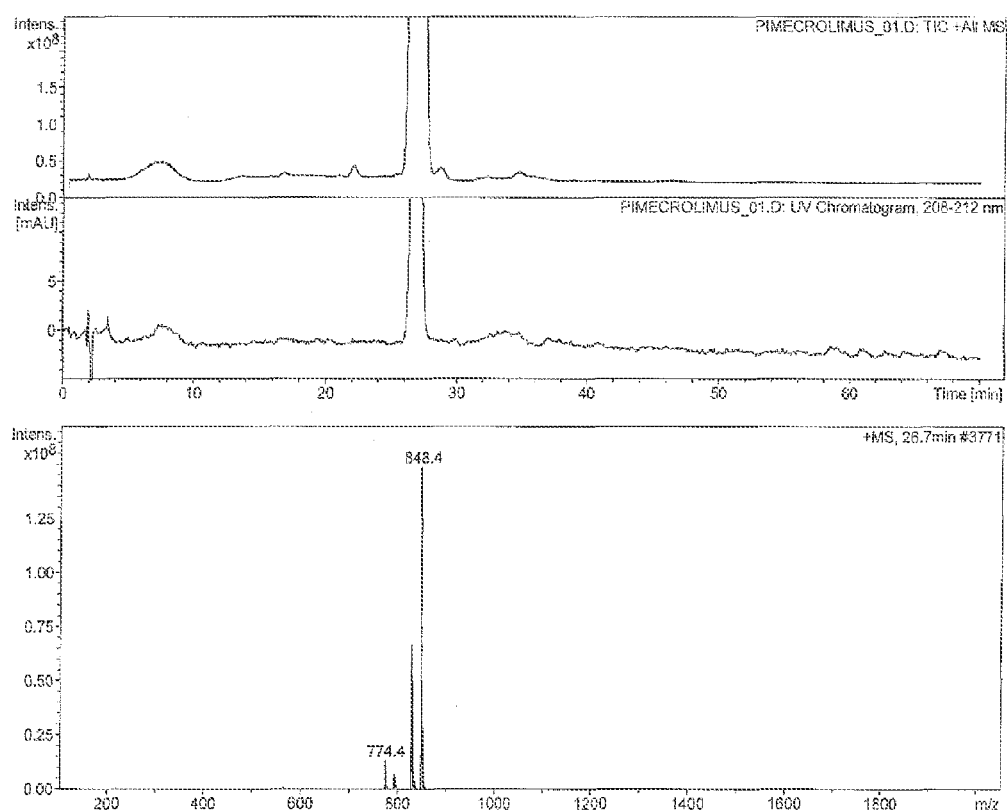
FIG. 12: HPLC/UV and HPLC/MS profiles of Pimecrolimus

FIG. 12. Pimecrolimus=the total ion current (TIC), the HPLC/UV profile and the mass spectrum of the main Pimecrolimus isomer eluted at 27'.

Figure 13:
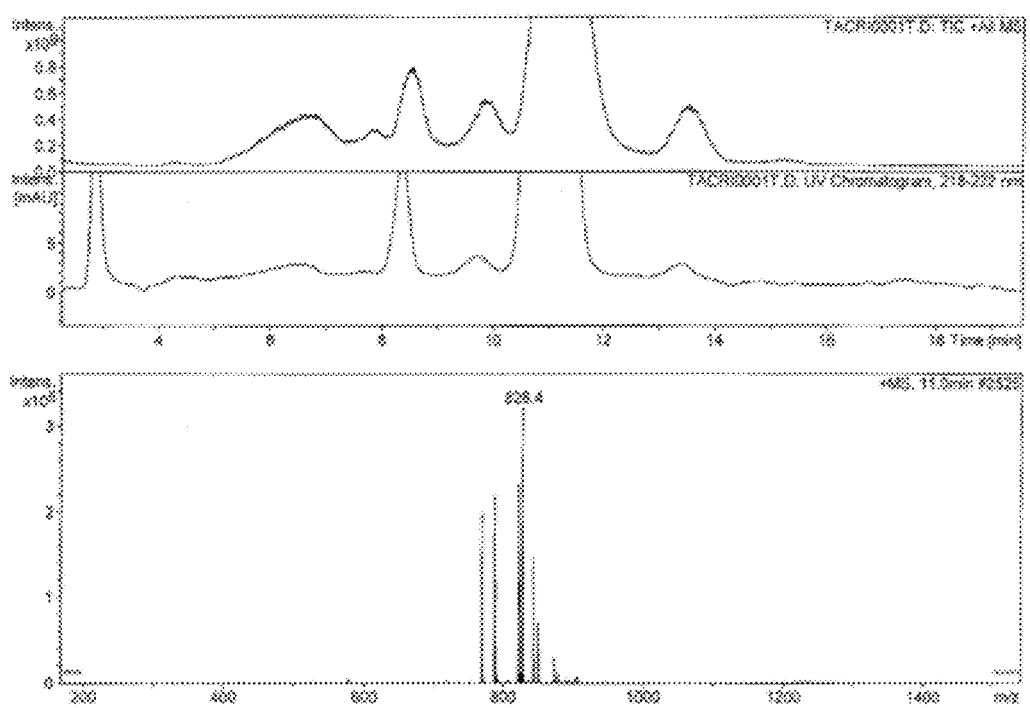
FIG. 13: HPLC/UV and HPLC/MS profiles of Tacrolimus
Figure 14:
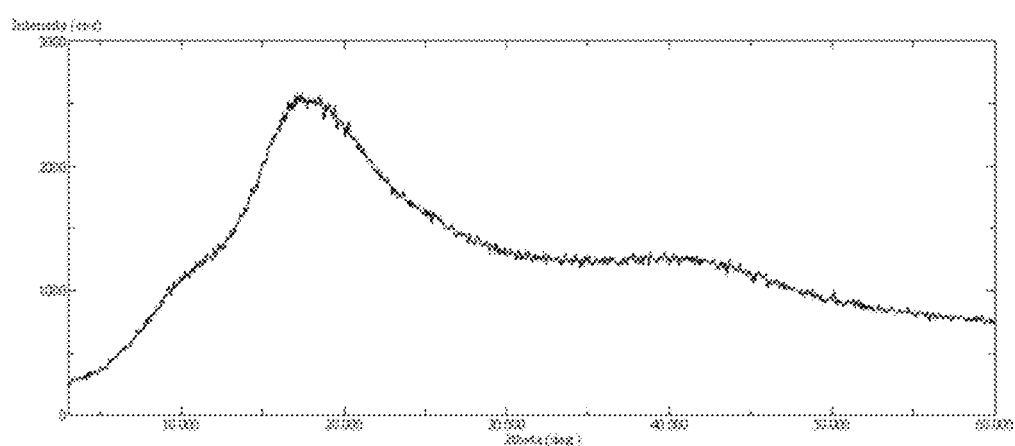
FIG. 14: DRX of Rapamycin (starting material) treated with spray dryer
Figure 15:
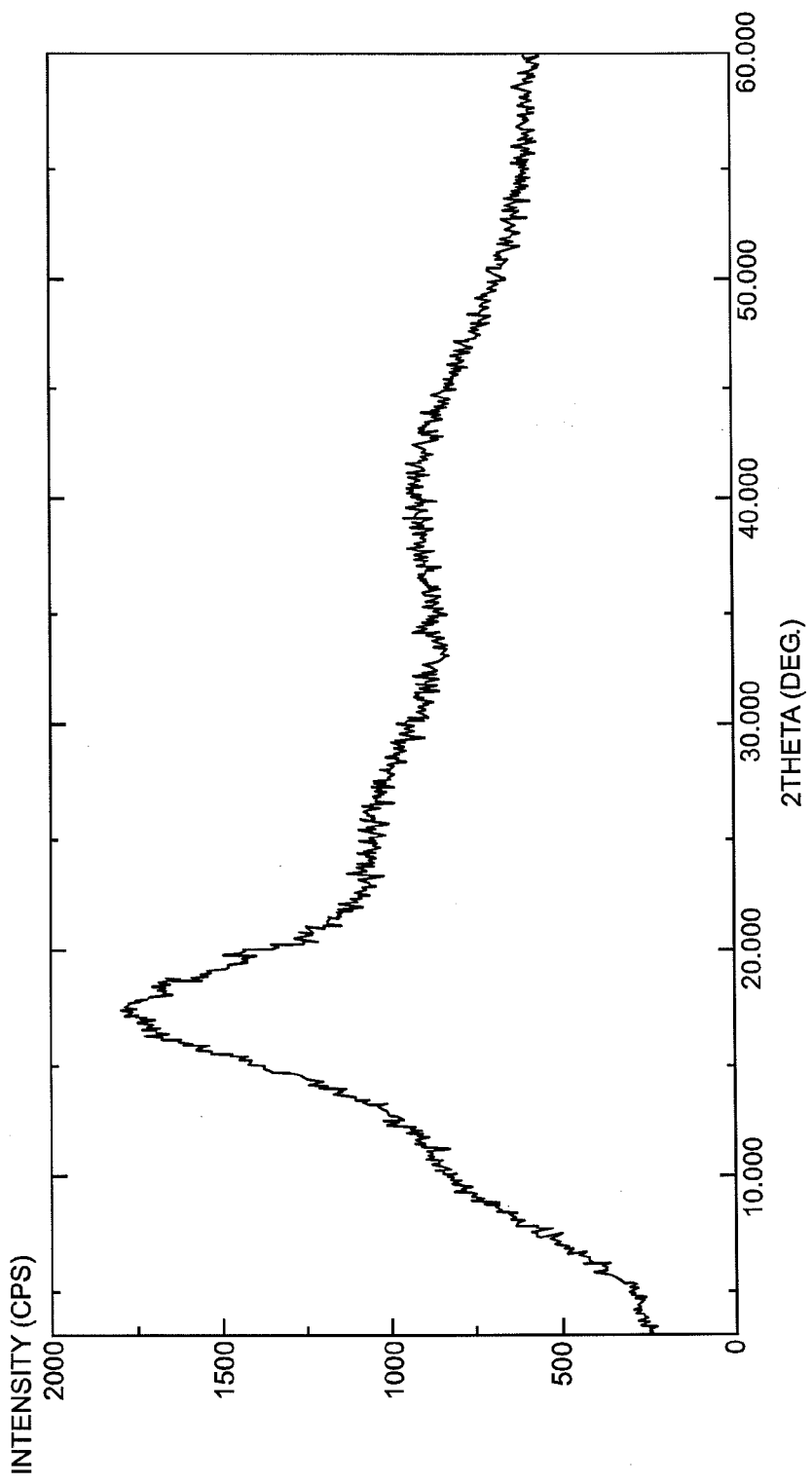
FIG. 15: DRX of Pimecrolimus (starting material) treated with spray dryer
Figure 16:
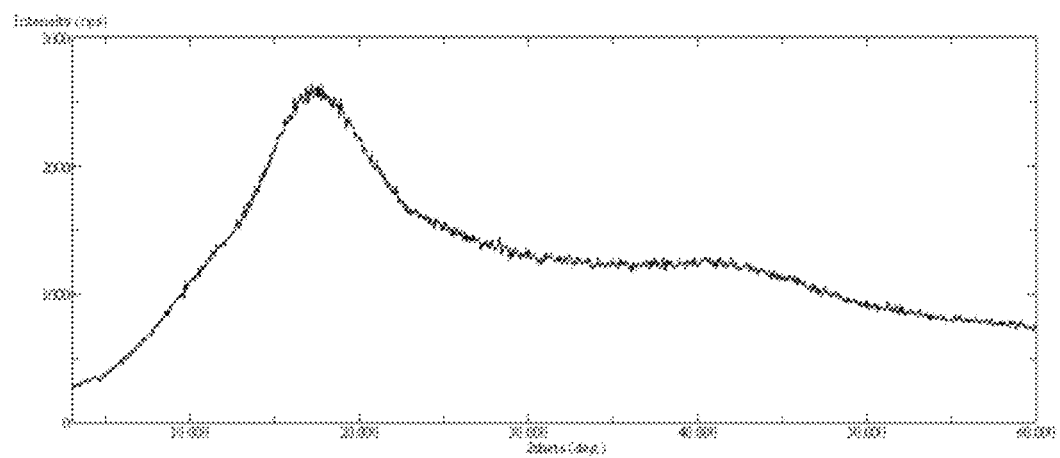
FIG. 16: DRX of Temsirolimus (starting material) treated with spray dryer
Figure 17:
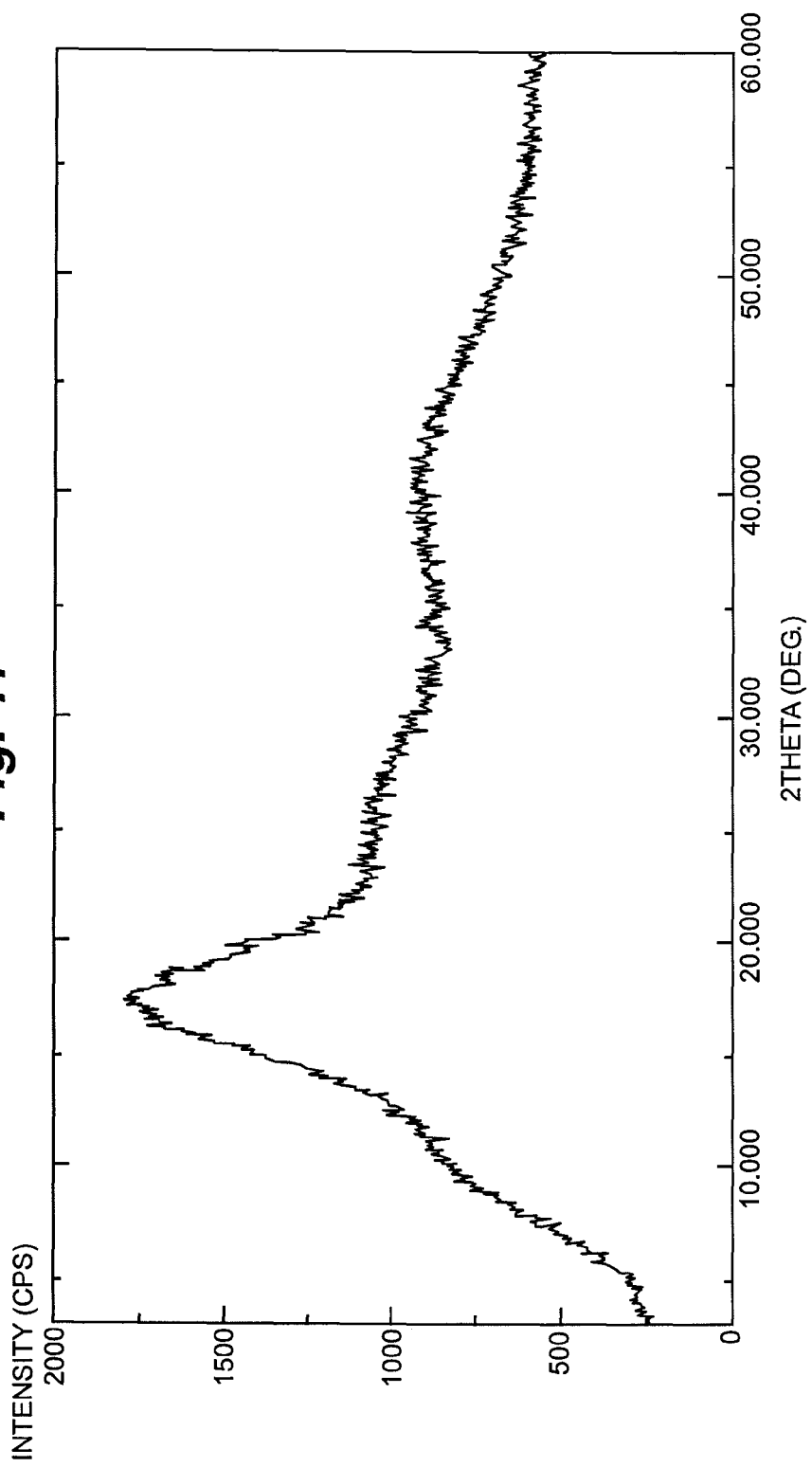
FIG. 17: DRX of Tacrolimus (starting material) treated with spray dryer
Figure 18:
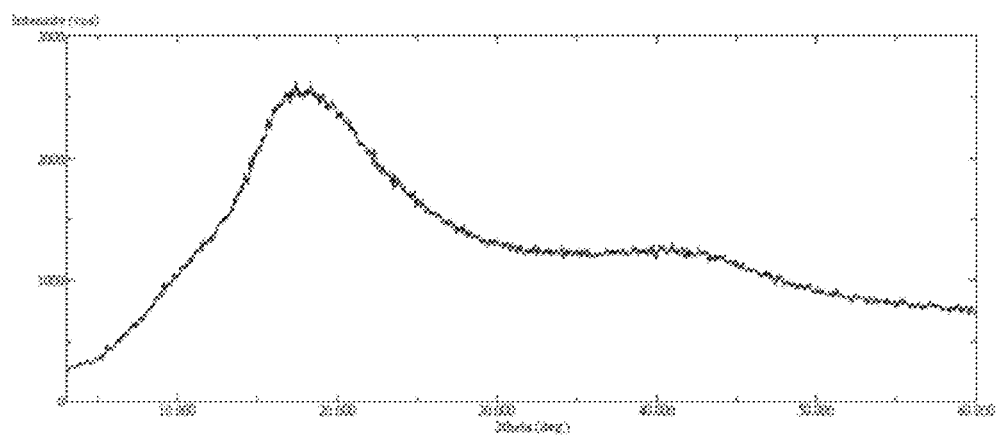
FIG. 18: DRX of Everolimus (starting material) treated with spray dryer
Figure 19:
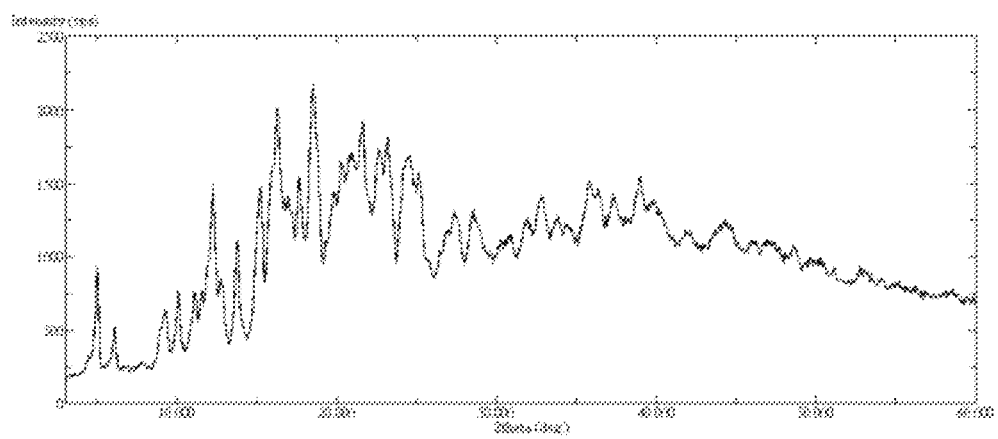
FIG. 19: DRX of gamma CD (starting material)
Figure 20:
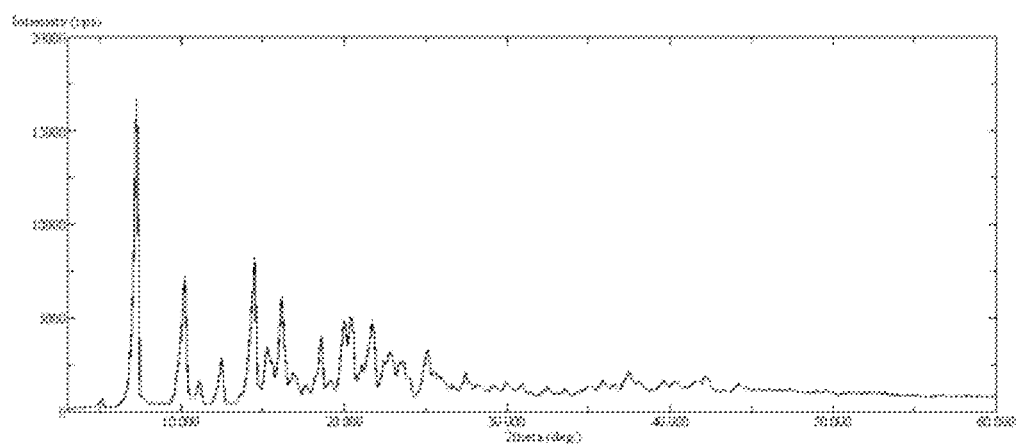
FIG. 20: DRX of crystalline Rapamycin (starting material)
Figure 21:
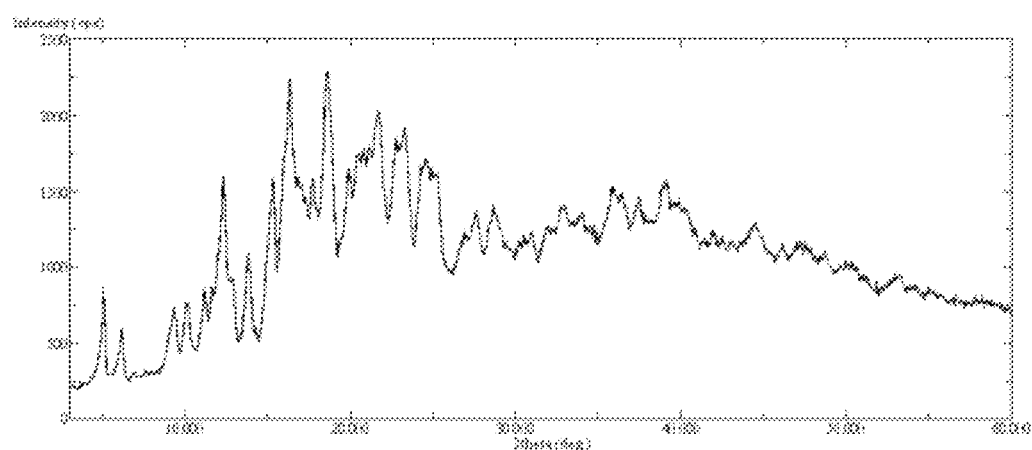
FIG. 21: DRX of Rapamycin gamma CD cyclodextrin complex
Figure 22:
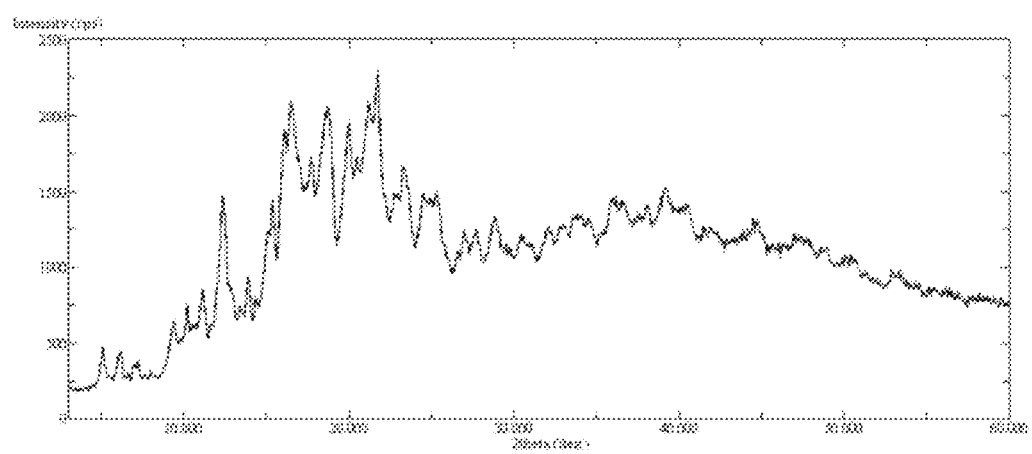
FIG. 22: DRX of a physical mixture of gamma CD and Rapamycin (0.6% w/w)
Figure 23:
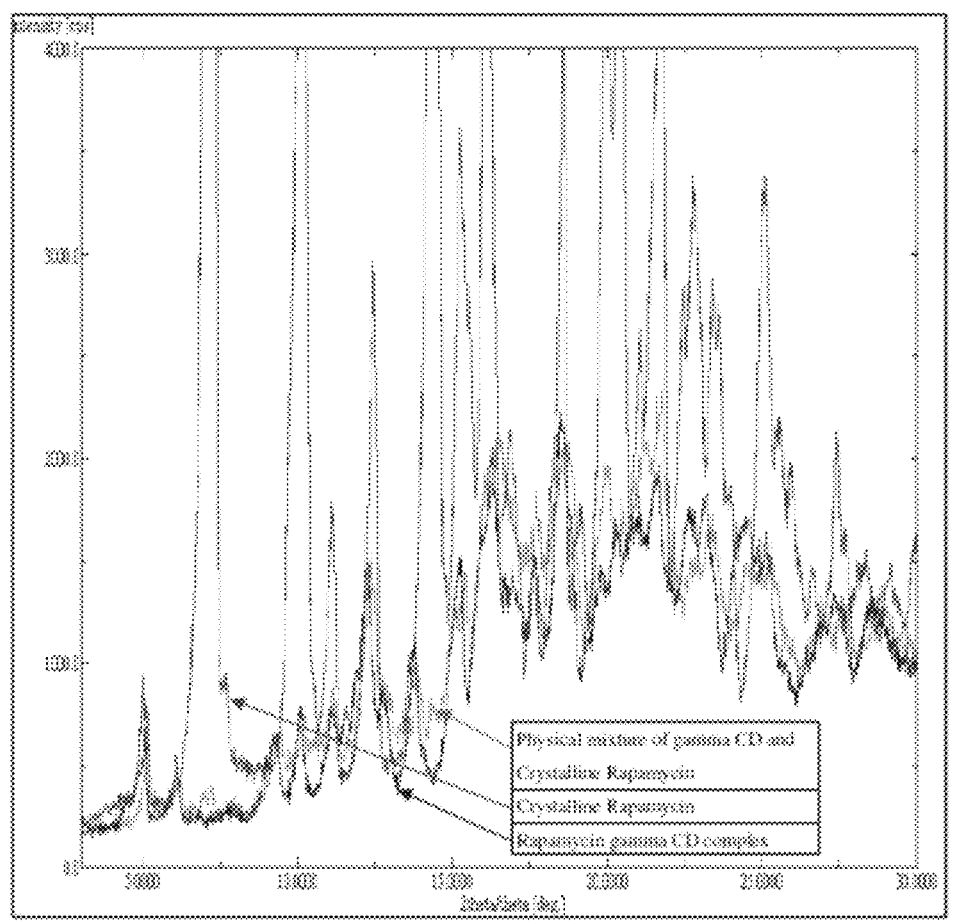
FIG. 23: Overlapped expanded DRX spectra, in the range of 3 and 30 2θ, of: a physical mixture of gamma CD and crystalline Rapamycin (0.6% w/w; in green colour), the DRX of crystalline Rapamycin (in red colour) and the DRX of Rapamycin gamma CD complex (in blue).

FIG. 13. Tacrolimus=the total ion current (TIC), the HPLC/UV profile and the mass spectrum of the main Tacrolimus isomer eluted at 11'0" (visible on the enclosed spectrum the water adduct a m/z=822 and the adduct with sodium with m/z=826).

Stability of Everolimus Complex with Gamma CD

The stability data on Everolimus complex with CD prepared according each of the examples 2 and 3 are reported on FIG. 3 and on Table 7.

In particular, in FIG. 3, are reported the sum of the related by products originated by degradation (HPLC data in area %) during a stability tests performed on the powder at 60° C. for 96 hours.

TABLE 7

Stability of Everolimus gamma CD/complex prepared using acetone versus amorphous Everolimus. In this table the sum of the related by products originated by degradation (HPLC data) during stability tests performed on the powder at 60° C. for 96 hours is reported.

| | Amorphous Everolimus (HPLC area % of total impurities) | Everolimus CD complex (HPLC area % of total impurities) |
|---|---|---|
| 0 | 1.5 | 1.59 |
| 24 | 2.44 | 1.79 |
| 48 | 4.52 | 1.87 |
| 72 | 7.1 | 1.99 |
| 96 | 9.2 | 2.17 |
| 168 | 14.1 | 2.62 |

Solid State of Gamma Rapamycin Complex, Gamma CD Everolimus Complex, Gamma CD Temsirolimus Complex, Gamma CD Tacrolimus Complex and Gamma CD Pimecrolimus Complex.

The solid state of Rapamycin crystalline after treatment with the spray dryer (or after evaporation from ethanolic or acetone solutions), of gamma CD (starting material), of Rapamycin gamma CD complex, of crystalline Rapamycin (starting material), and of Pimecrolimus, Temsirolimus, Tacrolimus and Everolimus after a spray dryer treatment (or after evaporation from ethanolic or acetone solutions) are reported in the FIGS. 14-23. These analyses confirm that after evaporation from ethanolic of acetonic solutions these macrolides are in an amorphous form. The DRX spectra of the complexes with gamma CD confirm that the crystalline phase of gamma CD is unchanged, as underlined in both FIG. 22 and table 9 below and, with the resolution of the employed technique, there is no trace of the macrolide in crystalline form.

TABLE 9

In this table the diagnostics 2θ values of a physical mixture of gamma CD and crystalline Rapamycin (0.6% w/w) and of a crystalline Rapamycin are reported. The first system in the physical mixture is splitted while on crystalline Rapamycin is a single reflection.

| Physical mixture of gamma CD and Crystalline Rapamycin (0.6%) | Crystalline Rapamycin |
|---|---|
| 6.94 e 7.20 2θ | 7.24 2θ |
| 14.32 2θ | 14.48 2θ |

The invention claimed is:

1. An inclusion complex comprising a dry powder comprising a macrolide and a gamma cyclodextrin, wherein the dry power is obtained by dissolving said macrolide in an organic solvent to obtain a solution, adding said gamma cytrodextrin to the solution and then evaporating the solution to obtain the dry power comprising said macrolide and said gamma cyclodextrin, wherein a weight ratio of said macrolide to said gamma cyclodextrin is between 1:100 and 1:400 and wherein said macrolide is selected from the group consisting of Rapamycin, Pimecrolimus, Temsirolimus, Everolimus, and Tacrolimus.

2. The complex according to claim 1, wherein said weight ratio between said macrolide and said gamma cyclodextrin is comprised between 1:111 and 1:333.

3. A method for the preparation of a inclusion complex comprising the following steps:
   a. dissolution of the macrolide in an organic solvent to obtain a solution;
   b. addition of said solution to gamma cyclodextrin;
   c. evaporation of the mixture;
   wherein the macrolide is selected from the group consisting of Rapamycin, Pimecrolimus, Temsirolimus, Everolimus, and Tacrolimus, and
   wherein a weight ratio of said macrolide to said gamma cyclodextrin in the complex is between 1:100 and 1:400.

4. The method according to claim 3, wherein the weight ratio of said macrolide to said gamma cyclodextrin is between 1:111 and 1:333.

5. The method according to claim 3, wherein said organic solvent is a polar organic solvent.

6. The method according to claim 5, wherein said polar organic solvent is selected from acetone, methanol and/or ethanol.

7. The method according to claim 3, wherein said evaporation is performed under vacuum, spray-drying, filtration and/or freeze-drying.

8. The method according to claim 7, wherein said filtration is performed by diluting with an organic solvent.

9. The method according to claim 8 wherein the organic solvent is an apolar organic solvent.

10. The method according to claim 8 wherein the organic solvent is a $C_5$-$C_8$ linear or branched hydrocarbon.

11. An inclusion complex obtainable by the method according to claim 3.

12. An inclusion complex obtainable by the method according to claim 5.

13. A pharmaceutical composition containing a complex according to claim 1 and at least one pharmaceutically acceptable excipient.

14. The composition according to claim 13, wherein said composition is a solid dosage form.

15. The composition according to claim 13, wherein said composition is an aqueous solution.

16. The composition according to claim 15, wherein said aqueous solution does not contain any organic solvent.

17. The composition according to claim 13, wherein the composition is for oral, ophthalmic, topical or parenteral use.

18. The composition according to claim 13 wherein the macrolide is Rapamycin.

\* \* \* \* \*